United States Patent [19]

Williams et al.

[11] 4,454,494

[45] Jun. 12, 1984

[54] OXYGEN SENSORS

[75] Inventors: David E. Williams; Bruce C. Tofield, both of Abingdon; Peter McGeehin, Newbury, all of England

[73] Assignee: Lucas Industries plc, Birmingham, England

[21] Appl. No.: 365,401

[22] Filed: Apr. 5, 1982

[30] Foreign Application Priority Data

Apr. 7, 1981 [GB] United Kingdom ................ 8110921

[51] Int. Cl.³ ............................................ G01N 27/12
[52] U.S. Cl. .................................... 338/34; 73/27 R;
422/94; 422/98; 423/594; 252/62.63
[58] Field of Search ....................... 338/34; 252/62.63;
423/594; 422/94, 98; 73/27 R

[56] References Cited

U.S. PATENT DOCUMENTS 3,535,245 10/1970 Lindquist ........................ 252/62.63
3,846,323 11/1974 Esper et al. ...................... 252/62.63
3,951,603 4/1976 Obayashi et al. ..................... 338/34
4,314,996 2/1982 Sekido et al. .......................... 338/34

FOREIGN PATENT DOCUMENTS 0055104 6/1982 European Pat. Off. .............. 422/94

Primary Examiner—Howard S. Williams
Assistant Examiner—Terryence Chapman
Attorney, Agent, or Firm—Trexler, Bushnell & Wolters, Ltd.

[57] ABSTRACT

An oxygen sensor which exhibits a change in electrical resistance as a function of oxygen partial pressure comprises at least one of strontium ferrate, barium ferrate and strontium barium ferrate, in which part of the iron in the ferrate lattice has been replaced by at least one element of valency greater than 3, such as titanium, cerium, niobium or tantalum.

13 Claims, 10 Drawing Figures

OXYGEN SENSORS

This invention relates to sensors for the measurement of oxygen partial pressures particularly, but not exclusively, in the exhaust gases of spark ignition internal combustion engines supplied with lean fuel/air mixtures, that is mixtures in which the fuel:air ratio is less than the stoichiometric combustion ratio of approximately 1:14 by weight.

It is known from British Pat. No. 1,231,140 that certain mixed valency oxide compounds with a significantly wide oxygen stoichiometry range, in particular alkaline earth ferrates and ferrites, exhibit a notable variation in electrical resistance as a function of changes in oxygen partial pressure, when operated at temperatures of about 350° C. The reason for this phenomenon is that the wide oxygen stoichiometry range means that, over a given oxygen partial pressure variation, the equilibrium between oxygen and the oxide compound may change substantially, with the compound being oxidised or reduced as a consequence. As disclosed in British Pat. No. 1,231,140, the oxidised and reduced forms of any particular mixed valency oxide compound, for example strontium ferrate ($SrFeO_{3-x}$), (where x is a variable and determines the degree of oxygen deficiency of the oxide, and its value depends upon temperature and oxygen partial pressure, but it generally falls within the range 0 to 0.5), may have different crystal structures separated by an intervening two-phase region in which the oxygen partial pressure is not thermodynamically defined as a function of the resistance or composition. As a result, it is suggested that difficulties may be met in using such an oxide sensor at temperatures and oxygen partial pressures which correspond to a two-phase region for the resistance element. The document exemplifies a temperature of 700° C. and an oxygen partial pressure of 1 Torr ($1.3 \times 10^{-3}$ atm.) in which, for a strontium ferrate sensor, the system will be in a two-phase region. As a possible means of overcoming the two-phase problem, British Pat. No. 1,231,140 suggests substitution of part of the iron in the oxide lattice by an element in oxide form, such as a rare earth oxide, including lanthanum and yttrium oxides.

In order to operate satisfactorily in the measurement of the oxygen partial pressures of the exhaust gases of spark ignition internal combustion engines using lean fuel/air mixtures, a mixed valency oxide sensor must obey a variety of criteria. It must not be degraded by the exhaust gases to which it is exposed, it must be stable between $-40°$ C. and $1000°$ C., and its behaviour should be restored rapidly after exposure to severely reducing conditions, e.g. an oxygen partial pressure of about $10^{-20}$ atm. Within these ranges, the sensor is most likely to experience an oxygen partial pressure of about $10^{-3}$ atm (corresponding to the exhaust gas produced by an engine operating with a lean fuel/air mixture) and a temperature of 700°–800° C. (corresponding to the temperature experienced near the exhaust manifold of a vehicle engine). It will, however, be appreciated from the preceding discussion that such oxygen partial pressures and temperatures fall exactly in the region where British Pat. No. 1,231,140 teaches that problems with two-phase regions are likely to result.

The relationship between oxygen partial pressure and the electrical conductivity of a mixed valency oxide sensor may be represented by the formula:

$$\sigma = A P_{O_2}^{\pm 1/n} \cdot e^{-E_a/kT}$$

where
- $\sigma$ is the electrical conductivity,
- A is a constant,
- $P_{O_2}$ is the oxygen partial pressure,
- n is a constant determined by the nature of the chemical equilibrium between oxygen and the sensor,
- $E_a$ is the activation energy which determines the temperature response of the conductivity, and, in general, incorporates contributions from the energies associated with defect formation, the generation of mobile charges and charge mobility itself,
- k is Boltzmanns constant, and
- T is the absolute temperature.

From the above equation, it will be seen that the lower the value of n, the greater is the sensitivity of the electrical conductivity to changes in oxygen partial pressure; and the lower the $E_a$ value, the lower is the sensitivity of the response to temperature fluctuations. Work conducted by the inventors on measuring the oxygen partial pressure of engine exhaust gases has shown that the conductivity in air of the sensor at 1000 K. should lie within the range $10^{-4}$ to 1 ohm$^{-1}$.cm$^{-1}$, n should be less than 6 and, between 773 K. and 1073 K., preferably should be less than or equal to 4, and $E_a$ should be less than 0.5 eV and preferably should be less than or equal to 0.2 eV.

Surprisingly, when investigating the possibility of using alkaline earth ferrates for the measurement of the oxygen partial pressure in the exhaust gases of spark ignition internal combustion engines operating on lean fuel/air mixtures, the inventors failed to encounter the phase change problem discussed in British Pat. No. 1,231,140. The reason for this different result is not understood and, since British Pat. No. 1,231,140 is silent with respect to the route used to prepare its sensor, it is difficult to suggest any explanation. Nevertheless, the results of the inventors' research showed that unsubstituted alkaline earth ferrates were not very suitable for measuring oxygen partial pressures in the exhaust emission from lean fuel/air mixtures. In particular, it was found that calcium ferrate had an n value of the order of 9, as compared with the maximum desirable value of 6, whereas barium ferrate was found to be unsuitable because its activation energy was strongly dependent on the oxygen partial pressure in the range of oxygen partial pressures corresponding to lean air/fuel ratios. Similarly, unsubstituted strontium ferrate suffered from the problems of having a high conductivity of about 9 ohm$^{-1}$.cm$^{-1}$ at temperatures in excess of 500° C. (although it was felt that this problem could be reduced by controlling the geometry of the sample), of requiring conditioning at high temperatures to ensure reproducible properties and having an activation energy similarly dependent on the oxygen partial pressure.

In an attempt to overcome the above-mentioned problems experienced with unsubstituted alkaline earth ferrates, an investigation was conducted into the effect of substitution in the lattice with a rare earth element (i.e. a trivalent element), such as lanthanum or yttrium, as taught by British Pat. No. 1,231,140. However, when lanthanum was substituted into the calcium ferrate lattice, it was found that the electrical conductivity became too high, rising to 17 ohm$^{-1}$.cm$^{-1}$ at 1000 K. In the case of the barium and strontium ferrate lattices, lanthanum substitution not only resulted in increased conductivity but also produced strong hysteresis in the variation in conductivity of the compound with temperature.

The substitution of yttrium into the barium and strontium ferrate lattices not only resulted in increased conductivity, but also reduced the sensitivity of the sensor to changes in oxygen partial pressure at the temperatures of interest so that the value of n was between 10 and 15 at 850° C.

An object of a particular aspect of the present invention is therefore to overcome or alleviate the above-mentioned problems experienced with oxygen sensors of the kind including an alkaline earth ferrate and to provide a sensor of this kind which can be used for the measurement of oxygen partial pressures in the exhaust gases of spark ignition internal combustion engines operating on lean fuel/air mixtures.

An object of another aspect of the present invention is to provide an oxygen sensor which can be used for stoichiometric and/or rich fuel/air mixtures.

In its broadest aspect, the present invention resides in an oxygen sensor exhibiting a change in electrical resistance as a function of oxygen partial pressure, comprising at least one of strontium ferrate ($SrFeO_{3-x}$), barium ferrate ($BaFeO_{3-x}$), and strontium barium ferrate ($Sr_{1-b}Ba_bFeO_{3-x}$), where x is as defined above and b is 0 to 1, in which part of the iron in the ferrate lattice has been replaced by at least one element of valency greater than 3.

In the case where said at least one element is a tetravalent element, preferably titanium or cerium, the substituted ferrate preferably obeys the formula:

$ZFe_{1-y}M_yO_{3-x}$, where Z is selected from Sr, Ba and $Sr_{1-b}Ba_b$, M is at least one tetravalent element, x is as defined above and y is greater than 0 but less than 0.9, preferably less than or equal to 0.7, and where b is as defined above. Preferably, where said tetravalent element is titanium or cerium, y is greater than or equal to 0.1 but less than or equal to 0.7.

In the case where said at least one element is a pentavalent element, preferably niobium or tantalum, the substituted ferrate preferably obeys the formula:

$ZFe_{1-y}Q_yO_{3-x}$, where Z and x are as defined above, Q is at least one pentavalent element, and y is greater than 0 but less than or equal to 0.7.

Where Q is niobium or tantalum in particular, it is preferred for y to be greater than or equal to 0.1 but less than or equal to 0.7. However, not all y values within the specified range will make suitable oxygen sensors for measurement in lean fuel/air mixtures at high temperatures (in the region of 1000 K.). For example, such sensors where y is 0.5 to 0.7 do not exhibit a sufficient change in electrical resistance in the lean fuel/air mixture region. Accordingly, y should be greater than 0 and less than 0.5 for lean fuel/air mixture oxygen sensors intended to operate at such high temperatures. On the other hand, we have found that, when y is greater than 0.5, the oxygen sensor can be used effectively for measurement in the lean fuel/air mixture region at temperatures below about 500° C.

In a particularly preferred oxygen sensor for lean fuel/air mixture operation, where the element is niobium or tantalum, the ferrate is barium ferrate, and y is greater than or equal to 0.25 but less than or equal to 0.33.

It is also possible to use a ferrate in which part of the iron has been replaced by at least one tetravalent element and by at least one pentavalent element, for example, a substituted ferrate of the formula $ZFe_{1-y}M_rQ_sO_{3-x}$, where Z, M, Q and x are as defined hereinabove, y is greater than 0 and less than or equal to 0.5, and $r+s=y$. In a convenient embodiment, $y=0.5$, and r and s are both 0.25.

Said element with valency greater than 3 may be partly replaced by a trivalent or divalent element.

Conveniently, said trivalent or divalent element is selected from aluminium, cobalt and nickel.

On testing, it was found that the oxygen sensor according to the invention is significantly less susceptible to the problems outlined above for unsubstituted alkaline earth ferrates and alkaline earth ferrates substituted with trivalent elements. In particular, the oxygen sensor of the invention is found to exhibit properties desirable for its application to the measurement of the oxygen partial pressure in the exhaust gases of spark ignition internal combustion engines operating with lean fuel/air mixtures. Furthermore, the oxygen sensor of the invention is found to exhibit properties desirable for its application to the measurement of the oxygen partial pressure in the exhaust gases of spark ignition internal combustion engines operating with stoichiometric or rich fuel/air mixtures. In addition, however, with the required temperature control, the sensor of the invention can be used at set temperatures between 250° C. and 900° C. to measure oxygen partial pressures in the range $10^{-3}$ atm to $2 \times 10^1$ atm making it useful in, for example, furnace atmosphere measurement.

BRIEF DESCRIPTION OF THE DRAWINGS

In the accompanying drawings.

The invention will now be more particularly described with reference to the accompanying drawings and the ensuing Examples.

EXAMPLE 1

A powder mixture was prepared consisting of 1 mole of barium carbonate of mean particle size 50 to 70 microns, 0.06 mole of tantalum oxide again of mean particle size 50 to 70 microns, and 0.44 mole of calcined ferric oxide of mean particle size 25 to 40 microns. Each of the samples was that supplied by British Drug Houses Ltd., as the reagent grade material and, before mixing, each sample was subjected to impurity analysis by spark emission spectrography. In the case of the barium carbonate, the main impurities were 0.3% by weight strontium, 200 ppm by weight calcium and 70 ppm by weight silicon, whereas in the case of the tantalum oxide, the major impurity was 44 ppm zirconium. The major impurities in the ferric oxide sample were 0.35% by weight calcium, 0.16% by weight chromium, 0.16% by weight silicon, 0.16% by weight zinc, 0.14% by weight lead, 700 ppm by weight aluminium, 460 ppm by weight nickel, 400 ppm by weight manganese, 280 ppm by weight molybdenum, and 100 ppm by weight tin.

The mixture was ball-milled in the presence of acetone in a synthetic resin pot using alumina balls for 12 hours to obtain a very homogeneous mix. The resultant mix was then dried at 100° C. for 2 hours to give a fine, homogeneously mixed powder which was ground and then passed through a 75 micron sieve. The powder was then placed in an alumina boat in a furnace which was slowly heated (i.e. of the order of up to 10° C. per minute) to 1200° C. in an air atmosphere. The furnace was held at this temperature for 12 hours, whereafter the product so formed was allowed to furnace cool to room temperature before being removed from the furnace. The product removed from the furnace was in the form of agglomerates and was ground before being subjectd to X-ray diffraction which showed that tantalum had entered the barium ferrate lattice. A sample of the ground powder was then placed in a tool steel die and punch assembly and cold pressed at 345 MNm$^{-2}$ into a cylindrical pellet 10 mm in diameter and 3.8 mm high. After removal from the die the pellet was sintered at 1200° C. for 24 hours and, when the pellet had cooled, electrical contact areas were provided on the planar end surfaces of the pellet. To produce the contact areas, a platinum paste was initially applied to the end surfaces, whereafter gold electrodes were attached and the assembly was fired at 1000° C. for four hours to effect joining of the electrodes.

Figure 1:
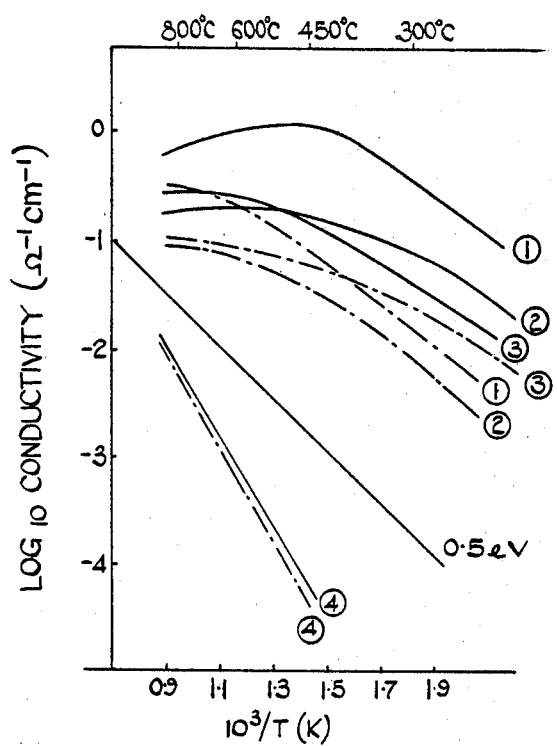
FIG. 1 is a graph plotting $\log_{10}$ conductivity ($ohm^{-1}.cm^{-1}$) against $10^3$/temperature, T(K.) for various barium tantalum ferrate compositions and at different oxygen partial pressures.

The resultant pellet was then mounted in an alumina jig and connected to an LCR bridge to enable electrical conductivity measurements to be made. The jig was then placed in a furnace and, with a constant air atmosphere being maintained in the furnace, the electrical conductivity of the sample was measured at varying temperatures between 300° C. and 1000° C. The results are shown in FIG. 1 by the continuous line numbered 1. The procedure was then repeated with the furnace atmosphere being maintained constant at an oxygen partial pressure of $1.2 \times 10^{-3}$ atm, with the results obtained being shown by the chain dotted line numbered 1 in FIG. 1.

By inspection of the gradient of the lines 1 in FIG. 1, it will be seen that the $E_a$ value for the sample was less than 0.5 eV for both atmospheres and over the entire temperature range investigated. In this respect, it is to be appreciated that the line marked "0.5 eV" is merely intended to show the gradient corresponding to an $E_a$ value of 0.5 eV and hence its position on the graph is arbitrary. It will also be seen from FIG. 1 that, for a given temperature, there was a noticeable difference between the electrical conductivity measured in air (corresponding to an oxygen partial pressure value of 0.21 atm) and the oxygen-depleted atmosphere (i.e. $1.2 \times 10^{-3}$ atm), particularly at the lower temperatures in the range investigated.

The procedure described above was then repeated for mixtures having different relative proportions of tantalum oxide and ferric oxide so as to vary the amount of tantalum substitution in the barium ferrate lattice. The composition of these further mixtures and the resultant ferrates are shown in Table 1 below:

TABLE 1

| Sample No. | $BaCO_3$ (mole) | $Ta_2O_5$ (mole) | $Fe_2O_3$ (mole) | Ferrate Composition |
|---|---|---|---|---|
| 2 | 1 | 0.125 | 0.375 | $BaFe_{\frac{3}{4}}Ta_{\frac{1}{4}}O_{(3-x)}$ |
| 3 | 1 | 0.167 | 0.333 | $BaFe_{\frac{3}{4}}Ta_{\frac{1}{4}}O_{(3-x)}$ |
| 4 | 1 | 0.25 | 0.25 | $BaFe_{\frac{3}{4}}Ta_{\frac{1}{4}}O_{(3-x)}$ |

The samples produced from the further mixtures given in Table 1 were subjected to the same electrical conductivity testing as the first-mentioned sample and the results are again shown in FIG. 1. As before, the continuous lines indicate the results obtained during testing in air, whereas the chain dotted lines indicate the results obtained in the oxygen-depleted atmosphere. In addition, each line in FIG. 1 is numbered in accordance with the number of its associated sample. From the graphs, it will be seen that both samples 2 and 3 had an $E_a$ value less than 0.5 eV.

In addition, it will be apparent that, for any given temperature over the entire range tested, each of samples 2 and 3 exhibited a readily detectable variation in electrical conductivity at the different oxygen partial pressures. In particular, in the case of sample 3, the variation in electrical conductivity was substantially constant throughout the temperature range. In the case of sample 4, however, the $E_a$ value was slightly in excess of 0.5 eV and there was only a small difference in electrical conductivity at the two oxygen partial pressure levels.

X-ray diffraction analysis of various tantalum ferrates ($BaFe_{\frac{3}{4}}Ta_{\frac{1}{4}}O_{3-x}$ and $BaFe_{\frac{3}{4}}Ta_{\frac{1}{4}}O_{3-x}$) showed that these materials as prepared were a mixture of two closely related phases. As the temperature of preparation of the compounds was raised from 1100° C., the two phases became more similar, and at temperatures in excess of 1300° C., single phase materials resulted. The electrical properties of the compounds were not substantially affected in respect of their variations with temperature and oxygen partial pressure by the presence of two phases but the behaviour became more reproducible when only a single phase was present.

The procedure of the first Example was repeated with starting materials from different suppliers (and hence having different impurities) but the results obtained showed no significant variation from those shown in FIG. 1.

EXAMPLE 2

The mixing, firing and testing procedure of Example 1 was repeated for 3 further samples but with the barium carbonate being replaced by strontium carbonate, again as supplied by British Drug Houses Ltd., as the reagent grade material and having a particle size of 50 to 70 microns. The composition of each mixture and the resultant ferrate sample are shown in Table 2 below and the results of the electrical conductivity testing are shown in FIG. 2.

TABLE 2

| Sample No. | SrCO$_3$ (mole) | Ta$_2$O$_5$ (mole) | Fe$_2$O$_3$ (mole) | Ferrate Composition |
|---|---|---|---|---|
| 1 | 1 | 0.125 | 0.375 | SrFe$_{\frac{3}{4}}$Ta$_{\frac{1}{4}}$O$_{(3-x)}$ |
| 2 | 1 | 0.167 | 0.333 | SrFe$_{\frac{3}{4}}$Ta$_{\frac{1}{4}}$O$_{(3-x)}$ |
| 3 | 1 | 0.25 | 0.25 | SrFe$_{\frac{1}{2}}$Ta$_{\frac{1}{2}}$O$_{(3-x)}$ |

Figure 2:
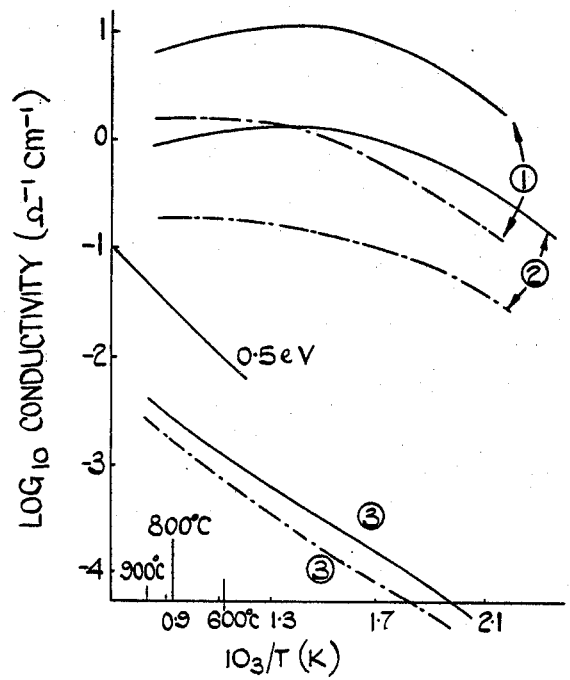
FIG. 2 is a graph similar to FIG. 1, but plotting the results obtained with various strontium tantalum ferrate compositions.

As in the case of FIG. 1, the continuous lines in FIG. 2 indicate the test results obtained in air, whereas the chain dotted lines indicate the results obtained in the oxygen-depleted atmosphere (oxygen partial pressure of $1.2 \times 10^{-3}$ atm). Moreover, each line is numbered with the number of its associated sample. From FIG. 2, it will be seen that each sample had an $E_a$ value less than 0.5 eV and that, for any given temperature over the entire range tested, samples 1 and 2 exhibited a substantial variation in electrical conductivity at the different oxygen levels. However, in the case of sample 3, the activation energy was substantially constant throughout the temperature range, but the specimen exhibited low conductivity variation with oxygen level over this range of oxygen partial pressure, making the material unsuitable for lean region sensing.

EXAMPLE 3

The procedure of Example 2 was repeated for three further samples, but in each case with the tantalum oxide replaced by titanium oxide, again as supplied by British Drug Houses Ltd., as the reagent grade material and with a particle size of 50-70 microns. The compositions of the various samples are shown in Table 3 below and the results of the electrical conductivity tests are shown in FIG. 3.

TABLE 3

| Sample No. | SrCO$_3$ | TiO$_2$ | Fe$_2$O$_3$ | Ferrate Composition |
|---|---|---|---|---|
| 1 | 1 | 0.25 | 0.375 | SrFe$_{\frac{3}{4}}$Ti$_{\frac{1}{4}}$O$_{(3-x)}$ |
| 2 | 1 | 0.5 | 0.25 | SrFe$_{\frac{1}{2}}$Ti$_{\frac{1}{2}}$O$_{(3-x)}$ |
| 3 | 1 | 0.9 | 0.05 | SrFe$_{0.1}$Ti$_{0.9}$O$_{(3-x)}$ |

Figure 3:
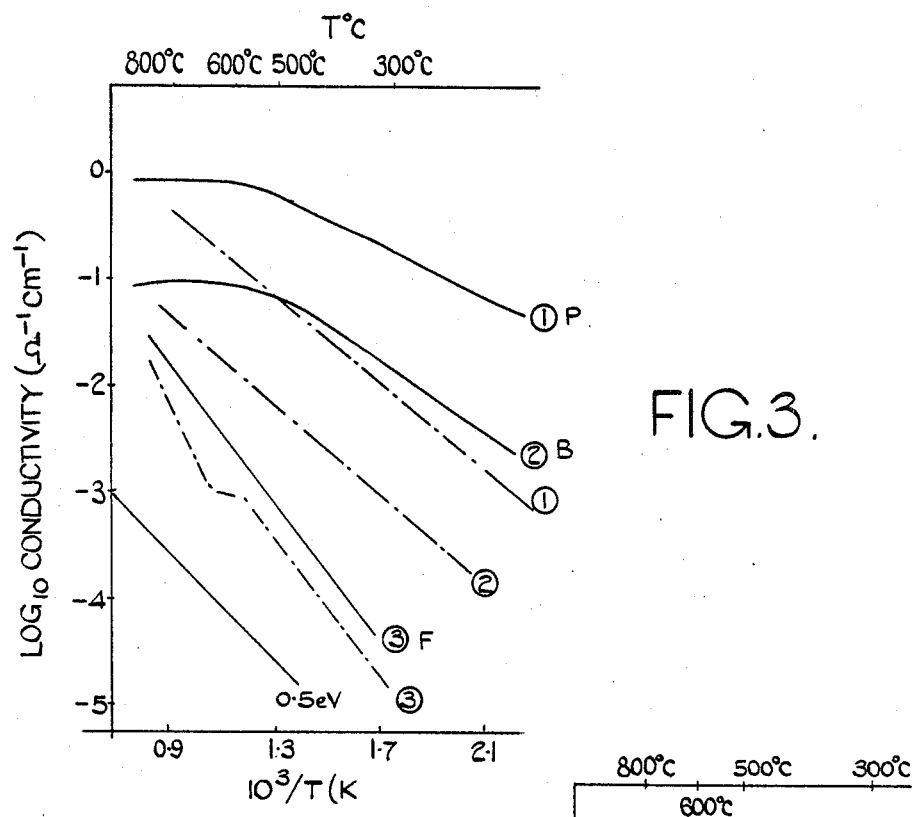
FIG. 3 is a graph similar to FIG. 2, but with titanium being used instead of tantalum as the substituent in the strontium ferrate lattice.

The nomenclature of FIGS. 1 and 2 is used in FIG. 3 from which it will be seen that, although at any given temperature all samples exhibited a substantial variation in electrical conductivity at the different oxygen partial pressure levels, sample 3 had an $E_a$ value in excess of 0.5 eV. The $E_a$ values for samples 1 and 2 were less than 0.5 eV.

X-ray diffraction analysis of the materials showed them to consist largely of one phase. Impurity phases present did not markedly alter the oxygen sensitivity or activation energy of the materials.

EXAMPLE 4

Figure 4:
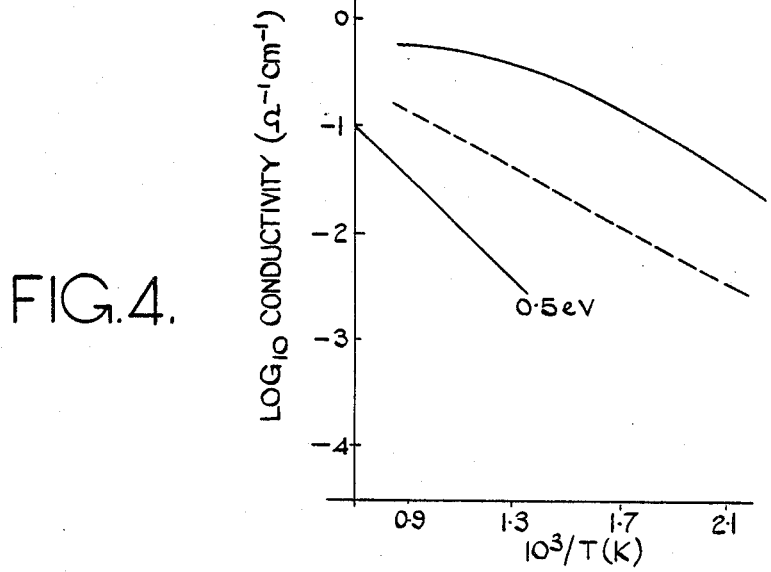
FIG. 4 is a graph similar to FIG. 1, but plotting the results obtained with a barium niobium ferrate composition.

The procedure of Example 1 was repeated with a starting mixture consisting of 1 mole of barium carbonate, 0.375 mole of ferric oxide and, in place of the tantalum oxide, 0.125 mole of niobium oxide. The barium carbonate and ferric oxide were the materials used in Example 1 and the niobium oxide was again the material supplied by British Drug Houses Ltd., as reagent grade, with an average particle size of 50 to 70 microns. The firing and electrical conductivity testing of the previous Examples were repeated, but with the oxygen-depleted atmosphere having a partial pressure of $1 \times 10^{-3}$ atm, and the results are shown in FIG. 4. Again the sample had an $E_a$ value less than 0.5 eV and, at any given temperature within the range investigated, exhibited a substantial variation in electrical conductivity at the two different oxygen partial pressure levels.

EXAMPLE 5

The procedure of the first Example was again repeated with three further starting mixtures, but in each case the starting mixture also contained a trivalent or divalent metal oxide. The composition of each starting mixture and the final ferrate are shown in Table 4 below and the results of the electrical conductivity testing are shown in FIG. 5.

TABLE 4

| Sample No. | BaCO$_3$ (mole) | Fe$_2$O$_3$ (mole) | Ta$_2$O$_5$ (mole) | Divalent or Trivalent Oxide | Ferrate Composition |
|---|---|---|---|---|---|
| 1 | 1 | 0.25 | 0.125 | 0.25 mole CoO | BaCo$_{\frac{1}{4}}$Fe$_{\frac{1}{2}}$Ta$_{\frac{1}{4}}$O$_{3-x}$ |
| 2 | 1 | 0.25 | 0.125 | 0.25 mole NiO | BaNi$_{\frac{1}{4}}$Fe$_{\frac{1}{2}}$Ta$_{\frac{1}{4}}$O$_{3-x}$ |
| 3 | 1 | 0.313 | 0.125 | 0.063 mole Al$_2$O$_3$ | BaAl$_{\frac{1}{8}}$Fe$_{\frac{5}{8}}$Ta$_{\frac{1}{4}}$O$_{(3-x)}$ |

Figure 5:
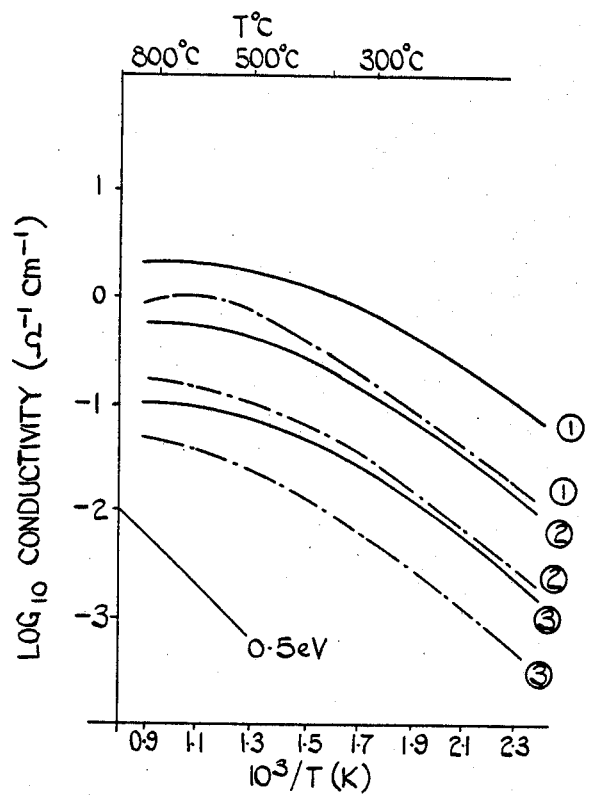
FIG. 5 is a graph similar to FIG. 1, but plotting the results obtained with a barium tantalum ferrate composition in which part of the tantalum has been replaced by various trivalent elements.

The same nomenclature as FIGS. 1 and 3 is used in FIG. 5 from which it will be seen that all the samples had an $E_a$ value less than 0.5 eV and at any given temperature exhibited a substantial variation in electrical conductivity in air and an oxygen-depleted atmosphere of $1 \times 10^{-3}$ atm.

It is to be appreciated that, although in each of the above Examples the starting mix was heated to 1200° C. to produce the required ferrate sensor, other firing temperatures can be employed and, with further examples a firing temperature of the order of 1300° C. was found to be the preferred temperature.

EXAMPLE 6

Figure 6:
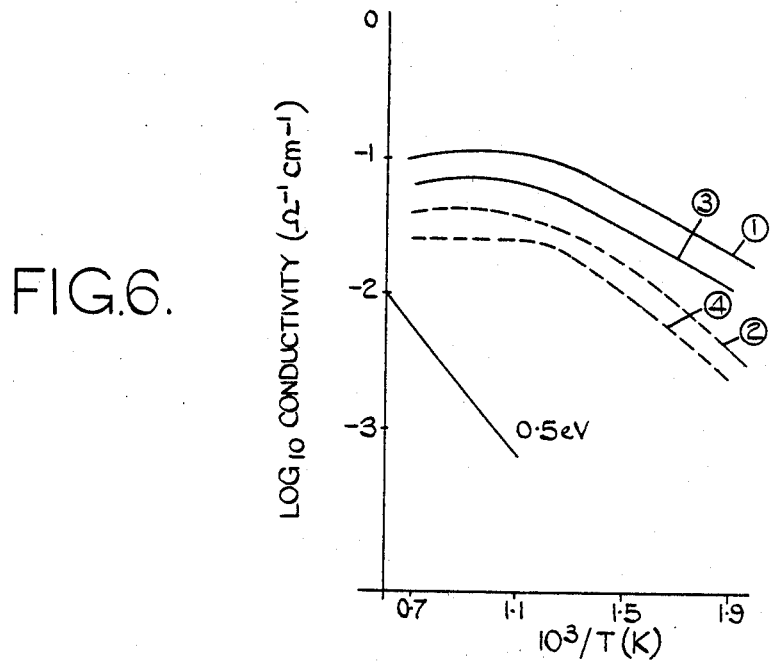
FIG. 6 is a graph similar to FIG. 1 plotting $\log_{10}$ conductance ($ohm^{-1}$) against $10^3$/Temperature (K.) for $BaFe_{\frac{1}{4}}Ti_{\frac{1}{4}}Ta_{\frac{1}{2}}O_{3-x}$ in pellet and thick film form in air (oxygen partial pressure 0.21 atm) and at an oxygen partial pressure of $1.2 \times 10^{-3}$ atm.

The procedure of Example 1 was repeated with a starting mixture of 1 mole barium carbonate, 0.25 moles titanium dioxide, 0.125 moles of tantalum oxide and 0.25 moles of ferric oxide. The materials used were those as described in Examples 1 and 3 and BaFe$_{\frac{1}{2}}$Ti$_{\frac{1}{4}}$Ta$_{\frac{1}{4}}$O$_{3-x}$ in the pellet form was produced. The results obtained are illustrated in FIG. 6 where curves 1 and 2 correspond to testing of the pellet in air (0.21 atm) and at $1.2 \times 10^{-3}$ atm respectively. This material was shown to have an $E_a$ value of less than 0.5 eV. It will be seen that, at any given temperature, there is a substantial variation in electrical conductivity at the two oxygen partial pressures.

EXAMPLE 7

A sample of the material prepared as described in Example 6 was pulverised to a powder of maximum particle size of 2.5 microns in an agate mortar (by hand). A 5 g sample of this powder was then mixed with 1.4 g of a commercially available printing medium Hanovia 4/628 supplied by Engelhard Industries to produce a viscous suspension, which was thinned slightly by the addition of 2 drops of terpineol supplied as reagent grade from Eastman Chemicals.

The suspension produced above was then printed onto clean, dense, 96% purity alumina substrates supplied by Kyocera of dimensions 48 mm long×6.5 mm wide×0.635 mm thick, using standard thick film technology or simply painting the suspension on to the alumina. The suspension was dried at 130° C. for 15 mins. in an oven with an air atmosphere, cooled, placed into a silica jig which in turn was placed in a furnace for firing the suspension. The furnace was heated at 10° C./min. to 600° C. and maintained at this temperature for 20-30 mins. An air atmosphere was maintained over the sensors, by flowing an oxygen/nitrogen mixture of 20:80 (volume %) at 500 cc/min.

The temperature of the furnace was then increased to 1250° C. at a rate of 10° C./min and maintained at this temperature for one hour whereafter the product was allowed to furnace cool to room temperature before being removed from the furnace. A gold paste type number T4248 supplied by Engelhard Industries was used to print electrodes to the ferrate material using standard thick film technology. The gold electrodes contacting both the ferrate and the alumina substrate. This material was then dried at 130° C. for 15 mins. in an oven, placed in a silica jig and fired as for the ferrate except the maximum temperature the furnace achieved was 900° C. and the product was only held at this temperature for 6 minutes.

Gold wires were attached to the gold thick film electrodes by a diffusion bonding process, the product was mounted into an alumina jig, placed in a furnace and connected to an LCR meter for electrical conductivity measurements to be made.

The results obtained are shown in FIG. 6 where curves 3 and 4 correspond to testing of the $BaFe_{\frac{1}{2}}Ti_{\frac{1}{4}}Ta_{\frac{1}{4}}O_{3-x}$ thick film in air (0.21 atm) and at $1.2\times10^{-3}$ atm, respectively. As can be seen, the material has an $E_a$ value of much less than 0.5 eV and a substantial variation in resistance at two different oxygen partial pressures, and is similar in behaviour to that of the material in pellet form.

EXAMPLE 8

The procedure for Example 7 was repeated for a ferrate composition as described in Example 3 (ie. $SrFe_{\frac{3}{4}}Ti_{\frac{1}{4}}O_{3-x}$). The results obtained for this composition are shown by curves 1 and 2, in FIG. 7 where curves 1 and 2 correspond to testing at 0.21 atm and 0.01 atm, respectively. The $E_a$ value is less than 0.5 eV and a substantial variation in resistance takes place at the two oxygen partial pressures. The results obtained for the thick film material are similar to those obtained for the same material in pellet form as shown by lines 1 in FIG. 3.

EXAMPLE 9

Figure 7:
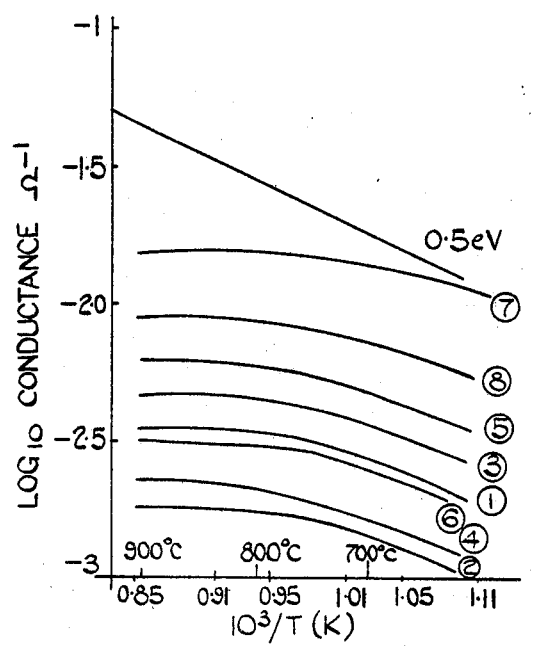
FIG. 7 is a graph plotting $\log_{10}$ conductance ($ohm^{-1}$) against $10^3$/Temperature (K.) for various strontium ferrate compositions at oxygen partial pressures of 21% $O_2$ (0.21 atm) and 1% $O_2$ (0.01 atm) where the materials ae in the form of thick film resistors supported on alumina substrates.

$SrFe_{\frac{1}{2}}Ta_{\frac{1}{4}}Co_{\frac{1}{4}}O_{3-x}$ in thick film form was prepared by the route outlined in Example 1 with a starting mixture of 1 mole of strontium carbonate 0.25 moles of ferric oxide, 0.125 moles of tantalum oxide and 0.25 moles of cobalt oxide. The resultant powder was subjected to the treatment outlined in Example 7. The results of the electrical conductivity testing are shown in FIG. 7 by curves 3 and 4 which correspond to testing at 0.21 atm and 0.01 atm, respectively.

The $E_a$ value is less than 0.5 eV and the resistance values change substantially at the two oxygen partial pressures used.

EXAMPLE 10

$Ba_{\frac{1}{2}}Sr_{\frac{1}{2}}Fe_{\frac{3}{4}}Ti_{\frac{1}{4}}O_{3-x}$ in thick film form was prepared by repeating Example 9 but using a starting mixture of 0.5 mole barium carbonate, 0.5 moles of strontium carbonate, 0.25 moles of titanium dioxide and 0.75 moles of iron oxide. The results of the electrical conductivity testing are shown FIG. 7 by curves 5 and 6 corresponding to testing at 0.21 atm and 0.01 atm, respectively.

EXAMPLE 11

$SrFe_{\frac{3}{4}}Ce_{\frac{1}{4}}O_{3-x}$ in thick film form was prepared by repeating Example 9, using a starting mixture of 1 mole strontium carbonate, 0.375 moles of ferric oxide, 0.25 moles cerium oxide all supplied by B.D.H. Ltd. The results of the electrical conductivity testing are shown in FIG. 7 by curves 7 and 8, corresponding to testing at 0.21 atm and 0.01 atm respectively.

EXAMPLE 12

Example 1 was repeated using appropriate molar quantities of the barium carbonate, ferric oxide and tantalum oxide used in Example 1 to obtain oxygen sensor pellets of $BaFe_{0.33}Ta_{0.67}O_{3-x}$, $BeFe_{0.4}Ta_{0.6}O_{3-x}$ and $BaFe_{0.45}Ta_{0.55}O_{3-x}$. Firing of the pellets was effected at 1350° C. for 12 hours in alumina crucibles lined with Pt. foil. Such pellets were n-type as opposed to barium tantalum ferrates of the formula $BaFe_{1-y}Ta_yO_{3-x}$ where y is less than 0.5, which are p-type. The conductivity activation energy of the pellets according to this Example at higher temperatures (greater than 500° C.) was a strong function of the oxygen partial pressure, being about 0.5 eV in 0.1% $O_2/N_2$ and 1.2 eV in 10% $O_2/N_2$. At lower temperatures (below 500° C.), the activation energy in 10% $O_2/N_2$ decreased to around 0.5 eV. At sufficiently higher temperatures, the conductivity did not vary with oxygen partial pressure, but as the temperature dropped the conductivity became very sensitive to oxygen partial pressure.

Although such pellets were not considered to be suitable for oxygen sensing in the exhaust gases of spark ignition internal combustion engines operating on lean fuel/air mixtures, it will be appreciated that they can be used for oxygen sensing at lower temperatures.

EXAMPLE 13

Example 1 was repeated but using appropriate molar quantities of the strontium carbonate, the titanium dioxide and the ferric oxide as used in Example 3 to produce oxygen sensor pellets of $SrFe_{0.4}Ti_{0.6}O_{3-x}$ and $SrFe_{0.3}Ti_{0.7}O_{3-x}$. Firing of the pellets was effected as described in Example 12 except for the $SrFe_{0.4}Ti_{0.6}O_{3-x}$ pellet which was fired at 1200° C. rather than 1350° C. The pellets produced in this example performed in a very similar manner to the previously described materials of the formula $SrFe_{1-y}Ti_yO_{3-x}$ where y=0.5 and 0.25. The conductivity activation energy in the 10% $O_2/N_2$ mixture was essentially zero at temperatures above about 500°-600° C. and conductivity at 850° C. varied roughly as $P_{O_2}^{1/5}$. These materials were p-type conductors. At 850° C., the conductivity in a 5% CO/5% $CO_2$/90%$N_2$ mixture (equivalent to an exhaust gas stream with an air-fuel ratio of about 11.5:1) was about one-tenth of that in 10%$O_2/N_2$.

While the materials of the invention have been exemplified as sensors of exhaust gas atmospheres of spark ignition internal combustion engines supplied with lean fuel/air mixtures, it is to be appreciated that the materials of the invention can be used in other applications. Conductivity changed rapidly with gas switches between oxidising and reducing atmospheres. It has been found that a conductivity minimum is exhibited at an oxygen partial pressure value of $10^{-10}$ atm at 850° C. This partial pressure is sufficiently close to the stoichiometric point of a fuel/air mixture so that such a material, when used in conjunction with a conventional sensor, for example titania, to indicate which side of stoichiometry a particular gas mixture lies, can provide a very sensitive control around the stoichiometric point and in rich fuel/air mixtures.

This can be achieved by feeding the output of the substituted ferrate sensor to an operational amplifier via gating means comprising the conventional sensor, such that the sign of the output amplifier indicates the side of the stoichiometric point on which the ferrate sensor is operating. Certain oxygen sensors according to the present invention can be made to exhibit a monotonic characteristic like a conventional titania sensor. An example of such a monotonic sensor according to the present invention is $BaFe_{\frac{2}{3}}Ta_{\frac{1}{3}}O_{3-x}$ whose characteristic is indicated by line 1 in FIG. 8. Such a sensor exhibits a sharp change in slope of the line 1 at an oxygen partial pressure of about $10^{-10}$ atm (the stoichiometric point of the fuel/air mixture in an internal combustion engine). The corresponding strontium tantalum ferrate is also found to exhibit such a monotonic characteristic. These monotonic sensors according to the present invention have the advantage that they exhibit an activation energy which is only about one-third that of a conventional titania sensor.

Figure 8:
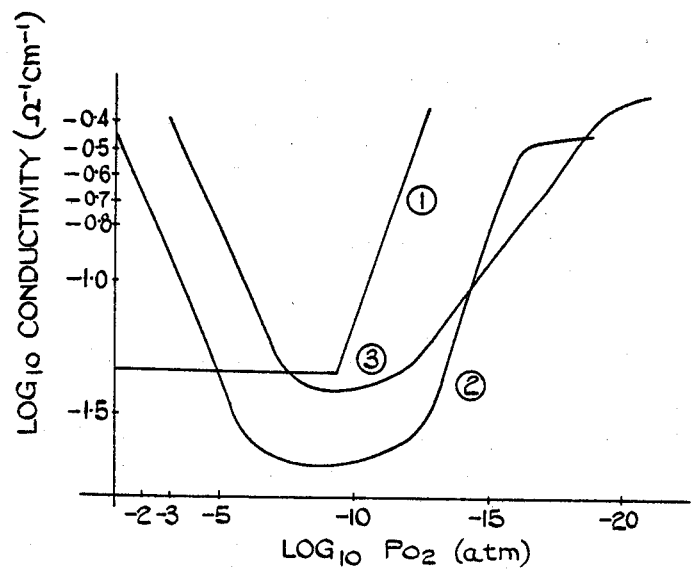
FIG. 8 is a graph showing the change in conductivity of various barium tantalum ferrate compositions as a function of the $\log_{10}$ oxygen partial pressure ($P_{O2}$)

Curves 2 and 3 in FIG. 8 relate to sensors according to the invention formed of $BaFe_{\frac{2}{3}}Ta_{\frac{1}{3}}O_{3-x}$ and $BaFe_{\frac{2}{3}}Ta_{\frac{1}{3}}O_{3-x}$, respectively. Such sensors are examples of those discussed hereinabove which exhibit a conductivity minimum at an oxygen partial pressure value of about $10^{-10}$ atm. at 850° C. Such characteristics have also been observed for other ferrates exemplified above.

It has been shown that, whilst at temperatures above 500° C., the sensors of the invention show substantially zero activation energy in the lean region, they show an activation energy of around 0.5 eV in the rich region. One consequence of this is that the rich region branch of curves such as 2 and 3 in FIG. 8 falls on the conductivity axis with falling temperature, whilst the lean branch remains substantially invariant. The conductivity minimum broadens, and shifts to lower values of both conductivity and oxygen partial pressure. Thus, as may be seen from FIG. 8, if a pellet of composition $BaFe_{\frac{2}{3}}Ta_{\frac{1}{3}}O_{3-x}$ is cycled between 10% $O_2/N_2$ and 5% $CO/5\%$ $CO_2/90\%$ $N_2$ at 850° C. (the latter being equivalent to an oxygen partial pressure of $10^{-17.5}$ atm corresponding to an air/fuel ratio of approximately 11.5:1), then apart from a transient charge when the gas is changed, only a small net change in conductivity results. However, at 700° C., the conductivity in the reducing gas is only one-fifth that in the oxidizing gas, whilst at 600° C., it is less than one-tenth. It will thus be appreciated that by appropriate choice of composition of material (eg by reference to Example 13) and by appropriate positioning of the sensor in the exhaust gas stream in order to obtain an appropriate range of setpoint temperatures below a chosen maximum, a sensor of the invention can be made to display the stoichiometric point of combustion without the need for an additional sensor.

A further consequence of the difference in activation energy in fuel-lean and fuel-rich conditions is that, by causing the heater which is used to control the operating temperature of the sensor to be switched with a mark/space ratio whereby the sensor is made to oscillate over a temperature excursion of eg. 50° C. about a mean value of 850° C. the conductivity change when the system is operating in the lean region will be substantially zero, whereas an excursion in conductivity will occur when operating in the rich region. Detection of substantially constant or of varying conductivity can therefore be used to detect and control at the stoichiometric point. Experiments performed on barium tantalum ferrate sensors according to the invention by repeatedly cycling between oxidizing and reducing conditions exhibited virtually little drift in conductivity values recorded. Thermal cycling between 860° C. and 650° C. again showed substantially zero drift.

Figure 9:
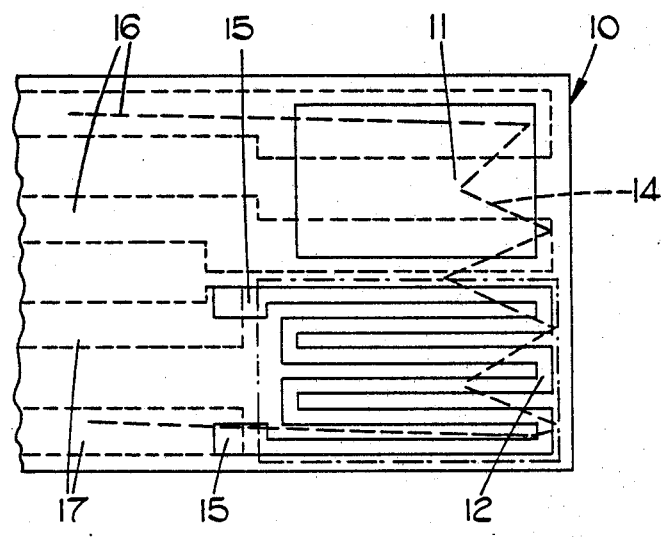
FIG. 9 is a plan view of part of a sensor device in which a sensor according to the invention is in the form of a thick film printed onto an alumina tile.

Referring now to FIG. 9, there is shown a thick film type of oxygen sensor assembly in which one end of a sintered alumina tile 10 supports an oxygen sensor 11 which is formed as a thick film thereon by the procedure described above in Example 7. A temperature sensor 12 and a heater 14 are also provided on said one end of the tile 10. The temperature sensor 12 is provided on the same major surface of the tile as the oxygen sensor 11 whilst the heater 14 is provided on the opposite major surface of the tile 10. The temperature sensor 12 has a terminal portion 15 at each end. First and second pairs of conductive areas 16 and 17 are printed onto the tile 11 to provide the necessary electrical connections with the oxygen sensor 11 and the temperature sensor 12, respectively. For a more detailed description of the assembly, attention is drawn to British Pat. No. 1,562,623, the disclosure of which is incorporated herein by reference.

Figure 10:
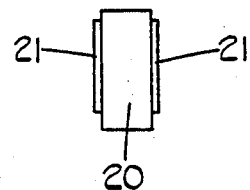
FIG. 10 is a plan view of a sensor device including a sensor according to the present invention in pellet form.

Referring now to FIG. 10, the oxygen sensor illustrated therein is produced as described in Example 1 above and comprises a body 20 formed of a pellet of the substituted ferrate material. The body 20 is of right cylindrical shape with a circular cross-section and has gold electrodes 21 secured to opposite axial ends thereof by a platinum paste (not shown). This oxygen sensor is arranged to be used by clamping it between a pair of spring loaded electrical contacts which engage the electrodes 21. The electrical contacts are mounted on a support which also carries a heater and a temperature sensor which, in use, are disposed adjacent the oxygen sensor.

We claim:

1. An oxygen sensor exhibiting a change in electrical resistance as a function of oxygen partial pressure, comprising at least one of strontium ferrate ($SrFeO_{3-x}$), barium ferrate ($BaFeO_{3-x}$), and strontium barium ferrate ($Sr_{1-b}Ba_bFeO_{3-x}$), where 3-x indicates an oxygen deficiency in the oxide and b is 0 to 1, in which 10 to 70 atomic percent of the iron in the ferrate lattice has been replaced by at least one element selected from the group consisting of titanium, cerium, tantalum and noibium.

2. An oxygen sensor as claimed in claim 1, wherein the ferrate obeys the formula: $ZFe_{1-y}M_yO_{3-x}$, where Z is selected from Sr, Ba and $Sr_{1-b}Ba_b$, M is element selected from the group consisting of titanium and cerium, 3-x indicates an oxygen deficiency in the oxide, and y is greater than or equal to but less than or equal to 0.7 and where b is as defined in claim 1.

3. An oxygen sensor as claimed in claim 1, wherein the ferrate obeys the formula: $ZFe_{1-y}Q_yO_{3-x}$, where Z is selected from Sr, Ba and $Sr_{1-b}Ba_b$, 3-x indicates an oxygen deficiency in the oxide, Q is selected from the group consisting of tantalum and niobium, and y is greater than or equal to 0.1 but less than or equal to 0.7.

4. An oxygen sensor as claimed in claim 3, wherein y is greater than or equal to 0.1 but less than or equal to 0.5, for use as a stoichiometric and/or rich fuel/air mixture sensor.

5. An oxygen sensor as claimed in claim 3, wherein y is greater than or equal to 0.1 but less than 0.5, for use as a lean fuel/air mixture sensor.

6. An oxygen sensor as claimed in claim 5, wherein y is greater than or equal to 0.25 but less than or equal to 0.33.

7. An oxygen sensor as claimed in claim 1, wherein part of the iron has been replaced by at least one tetravalent element selected from the group consisting of titanium and cerium and at least one pentavalent element selected from the group consisting of tantalum and niobium.

8. An oxygen sensor as claimed in claim 7, wherein the ferrate has the formula $ZFe_{1-y}M_rQ_sO_{3-x}$, where Z is selected from Sr,Ba and $Sr_{1-b}Ba_b$, M is said at least one tetravalent element, Q is said at least one pentavalent element, x is as defined herein, y is greater than or equal to 0.1 and less than or equal to 0.5, and $r+s=y$.

9. An oxygen sensor as claimed in claim 8, wherein y is 0.5, and each of r and s is 0.25.

10. An oxygen sensor as claimed in claim 1, wherein said element selected from the group consisting of tantulium and niobium is partly replaced by an element selected from a trivalent element and a divalent element.

11. An oxygen sensor as claimed in claim 10, wherein said element selected from a trivalent element and a divalent element is selected from aluminium, cobalt and nickel.

12. An oxygen sensor as claimed in claim 1, in the form of a pellet having electrodes attached thereto.

13. An oxygen sensor as claimed in claim 1, in the form of a film deposited on a substrate and having electrical connections thereto.

* * * * *

UNITED STATES PATENT AND TRADEMARK OFFICE
CERTIFICATE OF CORRECTION

PATENT NO. : 4,454,494

DATED : June 12, 1984

INVENTOR(S) : David Edward Williams, Bruce Cedric Tofield and Peter McGeehin

It is certified that error appears in the above-identified patent and that said Letters Patent is hereby corrected as shown below:

Column 4, line 59 change "ae" to --are--.

Column 10, line 66 change "of", first occurrence, to -- for --.

Column 12, line 7 change "C." to--C.,--.

Column 12, line 65 change "to but" to --to 0.1 but less--

Column 14, line 8, claim 10, after "consisting" insert -- of titanium, cerium, tantalum and niobium is partly replaced by an element selected from a trivalent element and a divalent element. --.

Signed and Sealed this

Twelfth Day of February 1985

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO. : 4,454,494
DATED : June 12, 1984
INVENTOR(S) : David Edward Williams, Bruce Cedric Tofield and Peter McGeehin It is certified that error appears in the above-identified patent and that said Letters Patent is hereby corrected as shown below:

Column 4, line 59 change "ae" to --are--.

Column 10, line 66 change "of", first occurrence, to --for--.

Column 12, line 7 change "C." to --C.,--.

Column 12, line 65 change "to but" to --to 0.1 but less--

Column 14, line 8, claim 10, after "consisting" should read --of titanium, cerium, tantalum and niobium is partly replaced by an element selected from a trivalent element and a divalent element. --.

This certificate supersedes certificate of correction issued February 12, 1985.

Signed and Sealed this

Twenty-second Day of October 1985

[SEAL]

Attest:

*Attesting Officer*

DONALD J. QUIGG

*Commissioner of Patents and Trademarks—Designate*